United States Patent [19]
Smith

[11] Patent Number: 5,947,990
[45] Date of Patent: *Sep. 7, 1999

[54] ENDOSCOPIC SURGICAL INSTRUMENT

[75] Inventor: Graham Smith, Plaistow, N.H.

[73] Assignee: Smith & Nephew, Inc., Andover, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/805,143

[22] Filed: Feb. 24, 1997

[51] Int. Cl.$^6$ .................................................. A61B 17/32
[52] U.S. Cl. ........................... 606/180; 606/170; 604/22
[58] Field of Search .................................. 606/170, 180; 604/22, 35

[56] References Cited

U.S. PATENT DOCUMENTS

| | | |
|---|---|---|
| 2,243,299 | 5/1941 | Travers . |
| 2,257,369 | 9/1941 | Davis . |
| 2,721,555 | 10/1955 | Jenney . |
| 3,294,085 | 12/1966 | Wallace . |
| 3,835,842 | 9/1974 | Iglesias . |
| 3,844,272 | 10/1974 | Banko .................................... 600/566 |
| 3,850,162 | 11/1974 | Iglesias . |
| 3,850,175 | 11/1974 | Iglesias . |
| 3,882,872 | 5/1975 | Douvas et al. . |
| 3,900,022 | 8/1975 | Widran . |
| 3,996,935 | 12/1976 | Banko . |

(List continued on next page.)

FOREIGN PATENT DOCUMENTS

| | | |
|---|---|---|
| 0 240 457 | 3/1987 | European Pat. Off. . |
| 0 286 415 | 10/1988 | European Pat. Off. . |
| 0 791 336 A1 | 8/1997 | European Pat. Off. . |
| 2 267 828 | 12/1993 | United Kingdom . |
| WO 92/03099 | 3/1982 | WIPO . |
| WO 96/32894 | 10/1996 | WIPO . |

OTHER PUBLICATIONS

Article entitled "Stop Clogging in Your Sinus Cases—Put our Typhoon Irrigated Cutter Blade in Your Handpiece," Trebay Medical Corp., 2 pages.

ENT Ear Nose & Throat Journal, "The Next Generation is Here—Introducing Hummer 2 ENT Micro Debrider," Jan., 1996, vol. 75, No. 1, 2 pages.

Razzak, Omar M. Abdel et al., "Rigid Ureteroscopes with Fiberoptic Imaging Bundles: Features and Irrigating Capacity," Journal of Endourology, vol. 8, No. 6, 1994, pp. 411–414.

Praeger, Donald L., "Praeger Irrigating Micro Intraocular Scissors," Ophthalmic Surgery, vol. 10, No. 7, Jul. 1979, pp. 33–35.

Bleasel, Kevin F. et al., "A new neurosurgical irrigating sucking cutter," J. Neurosurg 65:120–121, 1986.

Hayashi, Ken et al., "Corneal Endothelial Cell Loss Following Phacoemulsifications Using the Small–Port Phaco," Ophthalmic Surgery, vol. 25, No. 8, Aug. 1994, pp. 510–513.

Bailey, Paul F., "An irrigating instrument for inserting Simcoe and Binkhorst retropupillary lenses," Am Intra–Ocular Implant Soc. J., vol. II, Mar. 1985, pp. 187–188.

Vasquez, Jamie M., "Laparoscopic Ablation of Endometriosis Using the Cavitational Ultrasonic Surgical Aspirator," The Journal of American Asosciation of Gynecologic Laparoscopists, vol. 1, No. 1, Nov. 1993, pp. 36–42.

*Primary Examiner*—Michael Powell Buiz
*Assistant Examiner*—David O. Reip
*Attorney, Agent, or Firm*—Fish & Richardson P.C.

[57] ABSTRACT

An endoscopic surgical instrument is provided that includes a surgical implement, e.g., a cutting tool, and an irrigation device that supplies fluid to the surgical implement during use of the device. The endoscopic surgical instrument includes a surgical implement disposed at a distal region of the surgical instrument, and an irrigation device associated with the surgical implement in a manner to define a path for conveying irrigation fluid from a proximal region of the surgical instrument to the surgical implement.

19 Claims, 4 Drawing Sheets

U.S. PATENT DOCUMENTS

| | | |
|---|---|---|
| 4,167,943 | 9/1979 | Banko . |
| 4,301,802 | 11/1981 | Poler . |
| 4,517,977 | 5/1985 | Frost .......................................... 606/170 |
| 4,643,717 | 2/1987 | Cook et al. . |
| 4,650,461 | 3/1987 | Woods . |
| 4,650,463 | 3/1987 | LeVeen et al. . |
| 4,674,502 | 6/1987 | Imonti . |
| 4,678,459 | 7/1987 | Omik et al. ................................ 604/22 |
| 4,715,848 | 12/1987 | Beroza . |
| 4,844,088 | 7/1989 | Kambin . |
| 4,955,882 | 9/1990 | Hakky . |
| 5,019,036 | 5/1991 | Stahl et al. . |
| 5,163,433 | 11/1992 | Kagawa et al. . |
| 5,190,541 | 3/1993 | Abele et al. . |
| 5,217,479 | 6/1993 | Shuler . |
| 5,244,462 | 9/1993 | Delahuerga et al. . |
| 5,300,069 | 4/1994 | Hunsberger et al. . |
| 5,312,327 | 5/1994 | Bales et al. ................................ 604/21 |
| 5,322,505 | 6/1994 | Krause et al. . |
| 5,354,291 | 10/1994 | Bales et al. . |
| 5,403,276 | 4/1995 | Schechter et al. ......................... 604/22 |
| 5,403,317 | 4/1995 | Bonutti . |
| 5,405,348 | 4/1995 | Anspach, Jr. et al. ..................... 606/80 |
| 5,413,556 | 5/1995 | Whittingham . |
| 5,489,290 | 2/1996 | Furnish .................................... 606/170 |
| 5,505,210 | 4/1996 | Clement .................................... 128/753 |
| 5,569,254 | 10/1996 | Carlson et al. ............................ 606/79 |
| 5,709,698 | 1/1998 | Adams et al. ............................ 606/180 |
| 5,750,488 | 5/1998 | Wuchinich et al. . |

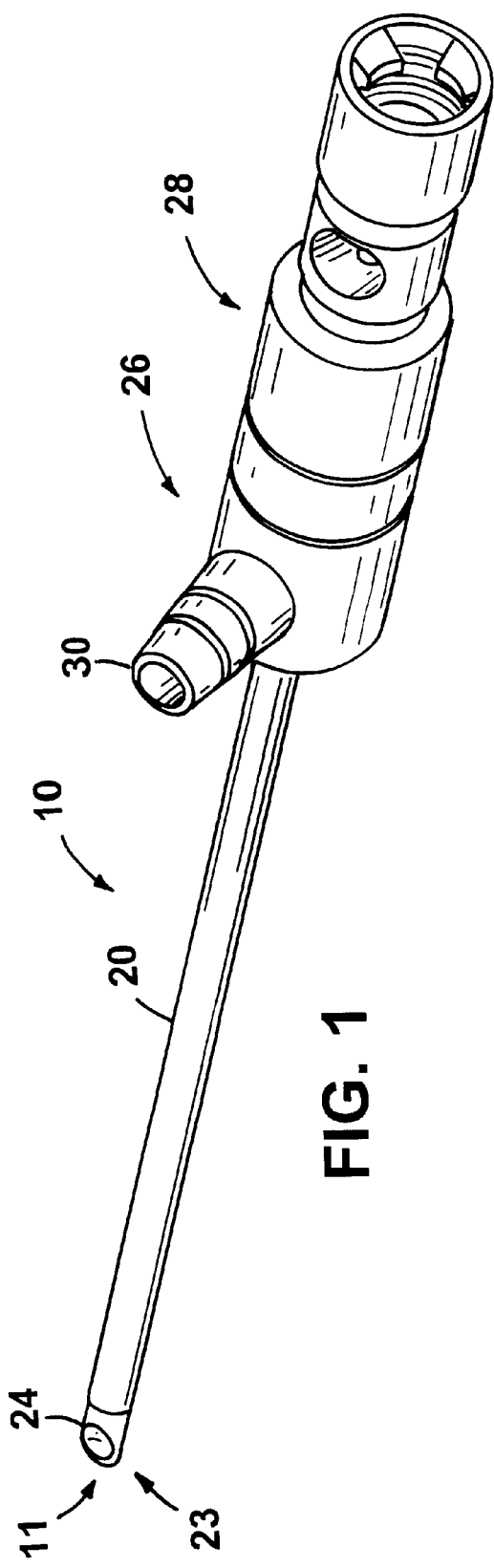
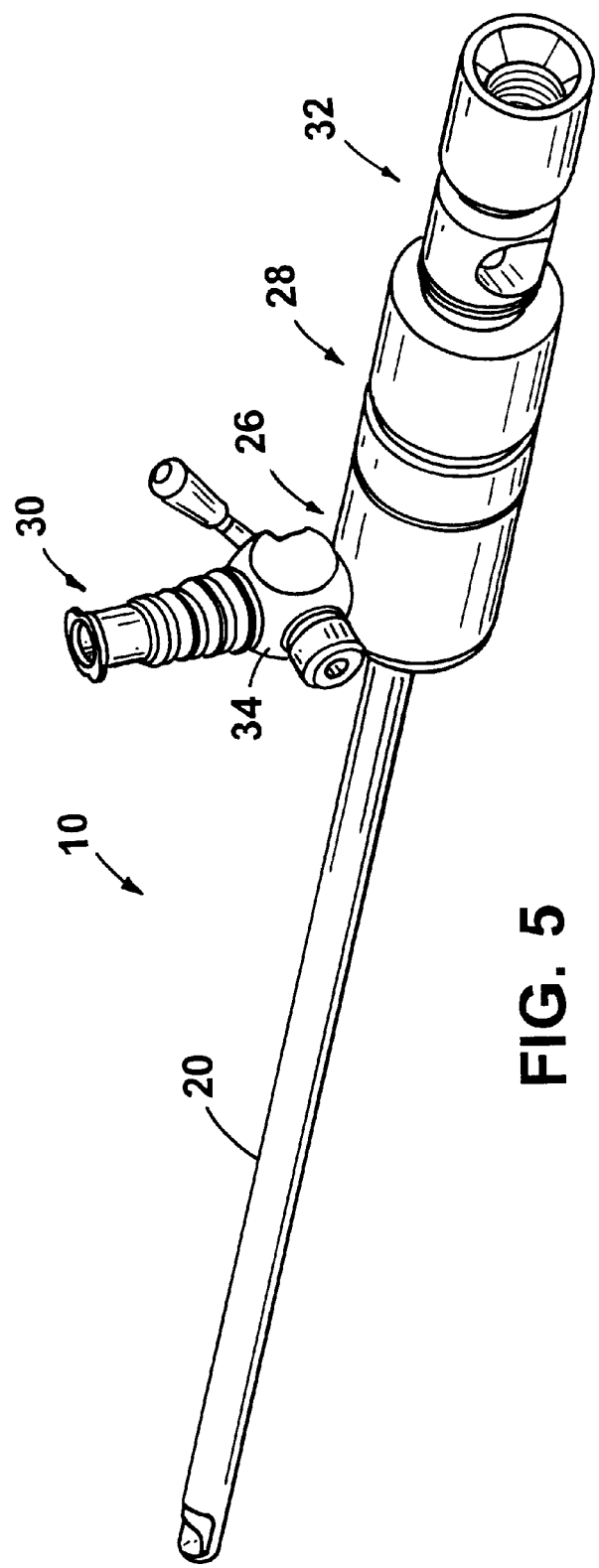

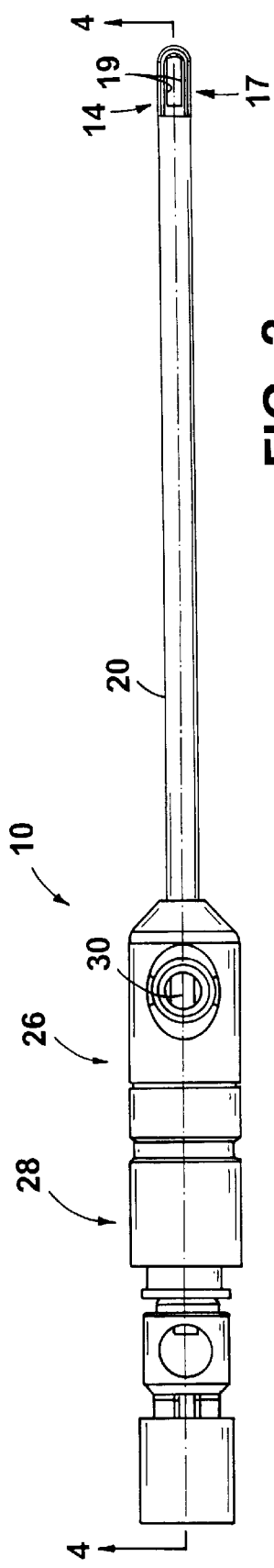
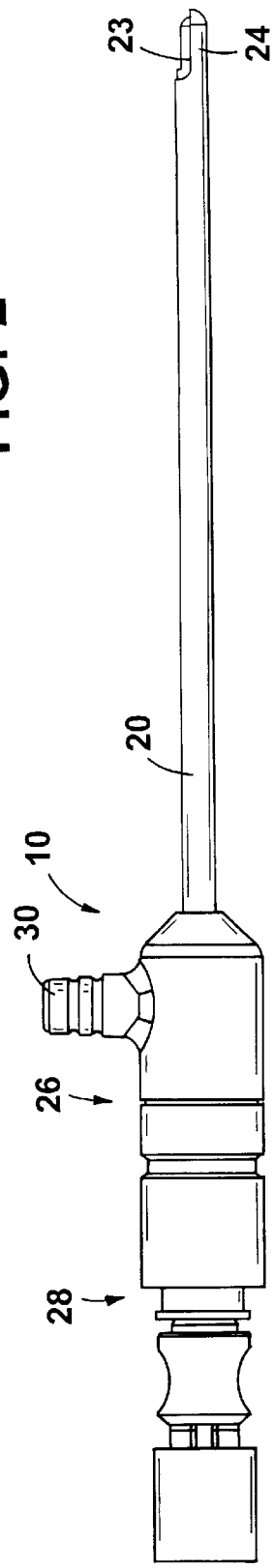
FIG. 2
FIG. 3

ENDOSCOPIC SURGICAL INSTRUMENT

BACKGROUND OF THE INVENTION

The present invention relates to endoscopic surgical instruments.

Several different kinds of surgical instruments have been developed for performing arthroscopic and other endoscopic surgical procedures. Some of these surgical instruments are powered, that is, operated by a motor; others are manual. Motor-driven instruments typically are received by a handpiece which houses the motor. Manual instruments are operated with a trigger-like handle. Examples of powered endoscopic surgical instruments are described in U.S. Pat. Nos. 4,203,444, 4,274,414, 4,834,729, 4,842,578, and 4,705,038; examples of manual endoscopic surgical instruments are described in U.S. Pat. Nos. 4,522,206 and 4,662,371. All of these patents are assigned to the present assignee and are incorporated herein by reference.

The instruments may include a wide variety of surgical implements for performing different types of surgical operations on body tissue. For example, some instruments are equipped with blades for cutting soft tissue, while others have burrs for abrading bone tissue. Still other implements (such as forceps and graspers) grip, rather than cut, tissue.

A typical cutting or abrading endoscopic, e.g., arthroscopic, surgical instrument includes a stationary outer tube within which an inner tube is moved (either manually or driven by a motor) during operation. The surgical implement is mounted to the distal end of the inner tube. Tissue or bone is exposed to the surgical implement through an opening in the distal end of the outer tube, and tissue and/or bone is cut by the moving implement. The cut tissue and bone fragments are drawn through the interior of the inner tube by suction applied at the proximal end of the instrument.

Endoscopic instruments are, whenever possible, used with irrigation devices, such as fluid pumps, which supply irrigating fluid to and suction fluid from the surgical site, as this improves cutting and transport of excised tissue and bone fragments from the surgical site.

Knee arthroscopy, which is performed in a closed capsule, where little danger exists of extravasation of fluid into adjacent anatomical structures, is carried out with the joint infused with saline. The use of fluid in this manner increases the cutting efficiency of powered resectors, and the transport of resected material from the joint. Some other areas of the body where tissue is routinely resected, however, are not generally amenable to infusion of saline. For example, in sinus surgery infusion of the sinuses with saline could potentially result in dangerous extravasation of fluid into the patient's airway.

SUMMARY OF THE INVENTION

The present invention provides an endoscopic surgical instrument which includes an irrigating device, eliminating the need for a separate irrigating device. This is particularly advantageous in applications, such as sinus surgery, where there is typically insufficient room at the surgical site for the placement of a separate irrigation device.

The invention, in one general aspect, features an improved endoscopic surgical instrument that includes a surgical implement disposed at a distal region of the surgical instrument, and an irrigation device associated with the surgical implement in a manner to define a path for conveying irrigating fluid from a proximal region of the surgical instrument to the surgical implement. The invention also features methods of using the instrument for endoscopic surgery, e.g., for sinus surgery.

Among other advantages, the invention allows the surgical instrument and the irrigation device to be introduced into the body together as a single surgical device (for example, through the same cannula during endoscopy). In addition to simplifying the surgical procedure, the invention reduces the trauma to the patient that accompanies the insertion of two separate instruments, and, as noted above, allows irrigating fluid to be introduced during surgery in very small areas, e.g., the patient's sinuses, where irrigation was hitherto typically difficult.

Moreover, in preferred embodiments the instrument of the invention delivers fluid directly to the surgical implement while simultaneously and continuously suctioning the fluid away at a sufficient rate so that fluid does not infuse the surgical site. Because fluid is delivered at the cutting blade, there is no need to infuse the entire surgical site. By reducing or eliminating the potential for extravasation, this feature advantageously allows the instrument to be used in applications, such as sinus surgery, in which the surgical site cannot safely be infused with saline.

In preferred embodiments, the endoscopic surgical instrument includes an outer tube with an opening at its distal region, an inner tube that rotates or otherwise moves within the outer tube, and a cutting implement, carried by the inner tube. Preferably, the irrigation device includes an irrigation sheath surrounding the outer tube to define a passage for fluid flow between the sheath and the outer tube. It is preferred that the irrigation sheath surround the surgical implement and have an opening at its distal region that is in communication with the opening in the outer tube. The irrigation sheath further includes a port, disposed in a proximal region of the sheath, for receiving irrigating fluid into the passage.

Other preferred embodiments include one or more of the following features. The endoscopic surgical instrument further includes a hub mounted at the proximal end of the outer tube, and the irrigation sheath includes an adaptor constructed to allow the irrigation sheath to be mounted onto the hub. The adaptor is bonded to the hub, e.g., by welding or adhesive. The adaptor includes a port for receiving fluid into the irrigation sheath. The port includes a valve to control fluid flow. The irrigation sheath is constructed of stainless steel or plastic. The outer diameter of the irrigation sheath in the region of the surgical implement is less than about 0.200", more preferably less than about 0.130". The clearance between the irrigation sheath and outer tube is less than 0.010", more preferably from about 0.008" to 0.010". The endoscopic surgical instrument is constructed to allow suction to be applied at the proximal end of the surgical instrument to remove fluid from the surgical site. Suction is applied through the inner tube.

The invention also features methods of using the surgical instrument.

Other features and advantages of the invention will become apparent from the following detailed description, and from the claims.

BRIEF DESCRIPTION OF THE DRAWINGS

FIG. 1 is a perspective view of an endoscopic surgical instrument with an outer irrigation sheath.

FIGS. 2 and 3 are top and side views, respectively, of the endoscopic surgical instrument shown in FIG. 1.

FIG. 5 is a perspective view of an endoscopic surgical instrument with an outer irrigation sheath and a stopcock to control fluid flow.

DESCRIPTION OF THE PREFERRED EMBODIMENTS

Figure 4:
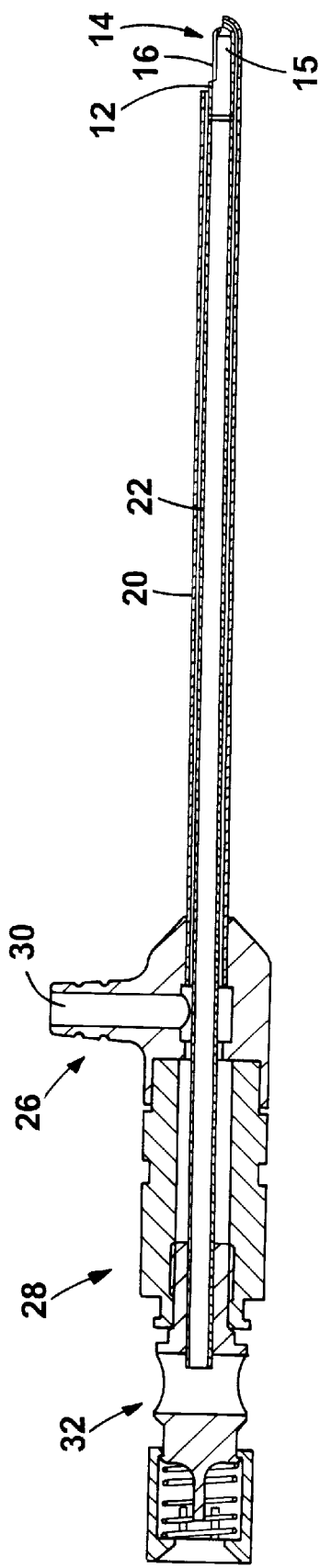
FIG. 4 is a side cross-sectional view of the endoscopic surgical instrument shown in FIG. 1, taken along line 4—4 in FIG. 2.

Referring to the figures, surgical instrument 10 includes a stationary outer tube 12 (FIG. 4) with a tissue-receiving opening 14 at its tip 15, an inner tube 16 that rotates or otherwise moves within outer tube 12, and a surgical implement 17 (FIG. 2) that cuts tissue admitted through the opening 14 in the outer tube. In this embodiment, the surgical implement consists of the sharp edges 19 of the inner tube 16, shown in FIG. 2.

Figure 1A:
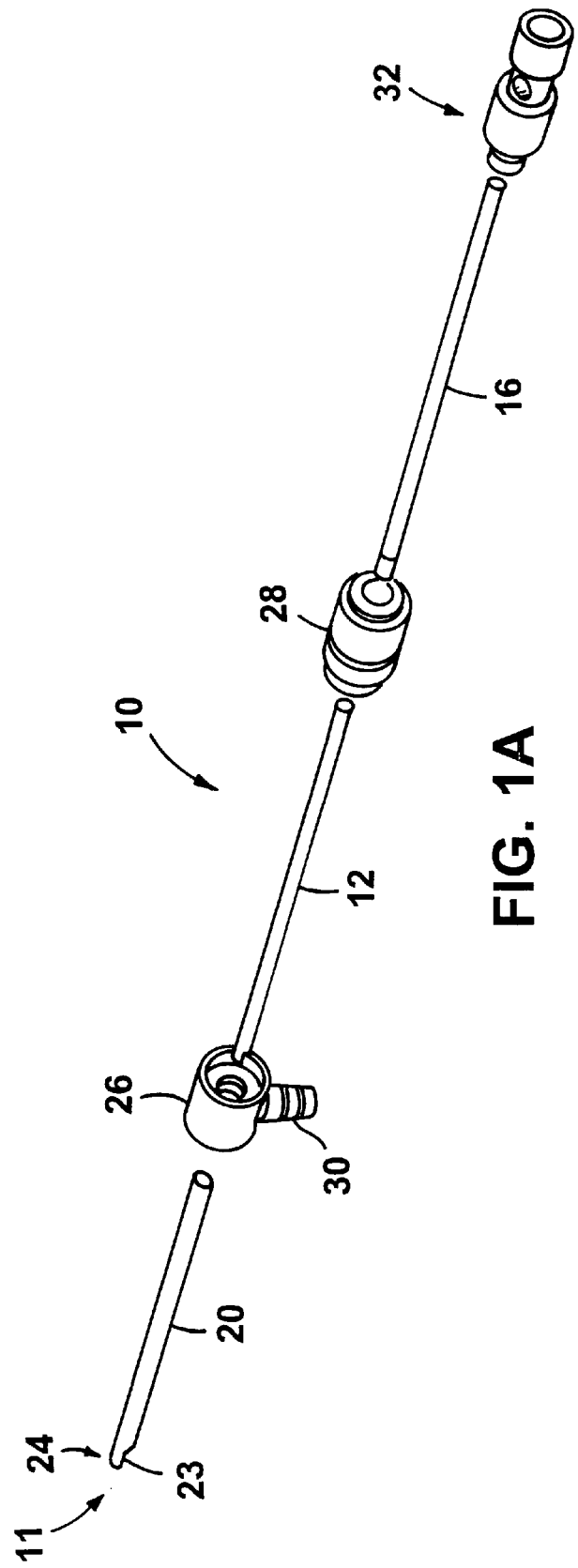
FIG. 1a is an exploded view of the endoscopic surgical instrument of FIG. 1.

Surgical instrument 10 further includes an irrigation sheath 20, surrounding outer tube 12. Irrigation sheath 20 defines an annular passage 22 for fluid flow between irrigation sheath 20 and outer tube 12. Irrigation sheath 20 includes an opening 23 (FIG. 1) at its distal tip 24 that is in communication with opening 14 in the stationary outer tube. Irrigation sheath 20 further includes an adaptor 26 at its proximal end. Adaptor 26 includes a side-facing port 30 for receiving irrigating fluid into the passage 22. Irrigating fluid is conveyed from port 30 to the distal tip 24 by passage 22, and is removed by suction (along with tissue and bone debris) through the interior of inner tube 16.

Adaptor 26 is dimensioned to be permanently attached onto the hub 28 of the surgical instrument, e.g., by ultrasonic welding, adhesive, or by being insert molded onto the hub. Hub 28 is typically formed of plastic, and is rigidly mounted at the proximal end of outer tube 12. Hub 28 rotatably receives drive shaft 32, which is rigidly mounted at the proximal end of inner tube 16.

The irrigation sheath 20 is constructed of stainless steel or plastic for strength and inertness. When surgical instrument 10 is to be used in a surgical application in which space is severely limited, e.g., sinus surgery, the distal end 11 of surgical instrument 10 has an outer diameter of less than about 0.130". To achieve this small outer diameter, irrigation sheath 20 has a wall thickness of less than 0.005", and the clearance between the inner wall of the irrigation sheath and the outer wall of the outer tube is less than 0.010", more preferably from about 0.0081" to 0.010".

As shown in FIG. 5, port 30 may include a stopcock 34, to allow control of the flow of fluid into irrigation sheath 20. Alternatively, other types of fluid-control valves may be used.

In operation, the surgical instrument is first assembled by placing inner tube 16 within outer tube 12, thereby moveably mounting drive shaft 32 in hub 28. Next, hub 28 is mounted in a handpiece (not shown) that includes a motor to turn drive shaft 32 and a device for applying suction through inner tube 16 to remove irrigation fluid and debris. The distal region 11 of surgical instrument 10 is then placed at the surgical site. When the surgeon wishes to use the surgical instrument, irrigation fluid is supplied through port 30 and removed by suction through inner tube 16, and the motor of the handpiece is activated to drive inner tube 16 and thus surgical implement 17.

Other embodiments are within the claims.

For example, adaptor 26 could be removably attached to hub 28. Hub 28 may be provided with a collar that extends distally and has a threaded interior surface that is spaced from the outer surface of outer tube 12. In this case, the proximal region 27 of the adaptor is compatibly threaded to engage the threads of the threaded collar, and is constructed to fit radially between the threaded collar of hub 28 and the outer surface of outer tube 12. Surgical instruments having a threaded hub are commercially available from Smith & Nephew Endoscopy Inc. of Andover, Mass.

Moreover, while the surgical instrument described above is a powered arthroscopic surgical instrument (that is, an instrument constructed to be driven by a motor, rather than by hand), the invention may also be used with manual instruments, as well as with other types of surgical instruments.

Additionally, while the surgical implement shown in the figures is a tissue-cutting tool, other surgical implements, e.g., other cutting tools, abrading tools, grasping tools, and the like, can also be used.

I claim:

1. An endoscopic surgical instrument comprising an outer member having a distal end and an opening at said distal end, a surgical implement movably disposed within said outer member at said opening, and an irrigation sheath through which said outer member extends to define a passage between said outer member and said sheath for conveying fluid from a proximal region of the surgical instrument to the distal end of the outer member, said sheath having a distal end that includes an opening configured to receive and at least partially surround said distal end of said outer member to define an outlet for the fluid adjacent to an edge of said opening of said outer member.

2. The endoscopic surgical instrument of claim 1 wherein said opening of said outer member is defined by a pair of side edges and a distal edge, said opening in said distal end of said sheath being configured to surround said side edges and said distal edge so that said outlet is defined adjacent to said side edges and said distal edge.

3. The endoscopic surgical device of claim 1 further comprising a hollow inner member that carries said surgical implement, said inner member having a port therein adapted to receive suction.

4. The endoscopic surgical instrument of claim 1 wherein said irrigation sheath includes a port, disposed in a proximal region of the irrigation device, for receiving fluid into the passage.

5. The endoscopic surgical instrument of claim 4 wherein said port includes a valve for controlling flow of fluid through said port.

6. The endoscopic surgical instrument of claim 1 further comprising a hub disposed at the proximal end of said outer member, and an adaptor constructed to allow the irrigation sheath to be mounted onto said hub.

7. The endoscopic surgical instrument of claim 6 wherein said adaptor includes a port constructed to receive fluid into the passage defined between said outer member and said irrigation sheath.

8. The endoscopic surgical instrument of claim 1 wherein the irrigation sheath comprises stainless steel.

9. The endoscopic surgical instrument of claim 1 wherein the irrigation sheath comprises plastic.

10. The endoscopic surgical instrument of claim 1 wherein the distal end of said irrigation sheath has an outer diameter of less than about 0.200".

11. The endoscopic surgical instrument of claim 10 wherein said distal end of said irrigation sheath has an outer diameter of less than about 0.130".

12. The endoscopic surgical instrument of claim 1 wherein there is a clearance between said irrigation sheath and said outer member, and said clearance is less than 0.010".

13. The endoscopic surgical instrument of claim 12 wherein said clearance is from about 0.008" to 0.010".

14. A method of performing endoscopic surgery comprising:
   (a) providing an endoscopic surgical instrument including
      an outer member having a distal end and an opening at said distal end,
      a surgical implement movably disposed within said outer member at said opening, and
      an irrigation sheath through which said outer member extends to define a passage between said outer member and said sheath for conveying irrigating fluid from a proximal region of the surgical instrument to the distal end of the outer member,
      said sheath having a distal end that includes an opening configured to receive and at least partially surround said distal end of said outer member to define an outlet for the fluid adjacent to an edge of said opening of said outer member;
   (b) introducing said surgical instrument into an area of the body of a patient;
   (c) conveying the irrigating fluid from the proximal region of the surgical instrument through the passage and out of the outlet into the area;
   (d) using the surgical implement to perform a surgical technique on the patient at the area.

15. The method of claim 14 wherein said instrument further includes a hollow inner member that carries said surgical implement, and further comprising withdrawing the irrigation fluid and tissue fragments produced by operation of the surgical implement from the area through said inner member.

16. The method of claim 14 further comprising suctioning the fluid from the area of the body of the patient at a sufficient rate so that the area is not infused with the fluid.

17. The method of claim 16 wherein said area of the patient's body is the sinus cavity.

18. An endoscopic surgical instrument comprising
   an outer member extending from a proximal region mounted to a hub to a distal end, said outer member having an opening at said distal end,
   a surgical implement carried by an inner member movably disposed within said outer member, said surgical implement being disposed at said opening, and
   an irrigation sheath through which said outer member extends to define a passage between said outer member and said sheath for conveying fluid from a proximal region of the surgical instrument to the distal end of the outer member,
   said sheath having a proximal end that is removably attachable to said hub, and a distal end that includes an opening configured to receive and at least partially surround said distal end of said outer member to define an outlet for the fluid adjacent to an edge of said opening of said outer member.

19. An irrigation device for use with endoscopic surgical instrument of the kind that includes an outer member having a distal end and an opening at said distal end, and a surgical implement movably disposed within said outer member at said opening, said irrigation device comprising
   an irrigation sheath configured to be attached to said surgical instrument and through which the outer member extends when the sheath is so attached to define a passage between the outer member and said sheath for conveying fluid from a proximal region of the surgical instrument to the distal end of the outer member,
   said sheath having a distal end that includes an opening configured to receive and at least partially surround the distal end of the outer member to define an outlet for the fluid adjacent to an edge of the opening of the outer member.

* * * * *

UNITED STATES PATENT AND TRADEMARK OFFICE
CERTIFICATE OF CORRECTION

PATENT NO. : 5,947,990

DATED : September 7, 1999

INVENTOR(S) : Graham Smith

It is certified that error appears in the above-identified patent and that said Letters Patent is hereby corrected as shown below:

Col. 3, line 47, replace "0.0081"" with --0.008--.

Signed and Sealed this

Twenty-sixth Day of September, 2000

Attest:

Q. TODD DICKINSON

Attesting Officer

Director of Patents and Trademarks